US012642540B2

(12) United States Patent
Aksu

(10) Patent No.: US 12,642,540 B2
(45) Date of Patent: Jun. 2, 2026

(54) BONE FIXATION SYSTEM FOR SACROILIAC JOINT AND RELATED METHODS

(71) Applicant: Kenan Aksu, Exton, PA (US)

(72) Inventor: Kenan Aksu, Exton, PA (US)

( * ) Notice: Subject to any disclaimer, the term of this patent is extended or adjusted under 35 U.S.C. 154(b) by 631 days.

(21) Appl. No.: 18/108,255

(22) Filed: Feb. 10, 2023

(65) Prior Publication Data

US 2023/0301665 A1      Sep. 28, 2023

Related U.S. Application Data

(60) Provisional application No. 63/323,301, filed on Mar. 24, 2022.

(51) Int. Cl.
    *A61B 17/17*        (2006.01)
    *A61B 17/68*        (2006.01)
    *A61F 2/30*         (2006.01)
(52) U.S. Cl.
    CPC .............. *A61B 17/17* (2013.01); *A61B 17/68* (2013.01); *A61F 2002/30995* (2013.01)
(58) Field of Classification Search
    CPC ........................................... A61F 2002/30995
    See application file for complete search history.

(56) References Cited

U.S. PATENT DOCUMENTS 5,827,285 A * 10/1998 Bramlet ................. A61B 17/80
                                                606/328
9,724,149 B2    8/2017 Trieu et al.

9,788,862 B2   10/2017 Mootien et al.
9,949,843 B2    4/2018 Reiley et al.
2014/0031934 A1*  1/2014 Trieu ................. A61B 17/8685
                                                623/17.11
2016/0135861 A1*  5/2016 Kollmer ................. A61B 50/20
                                                606/324
2016/0175113 A1   6/2016 Lins
2016/0302941 A1* 10/2016 Reiley ................ A61B 17/7055
2016/0310197 A1  10/2016 Black et al.
2020/0138485 A1*  5/2020 Kuwamura ......... A61F 2/30988

FOREIGN PATENT DOCUMENTS

WO        2006124987 A1   11/2006
WO        2017127235 A1    7/2017

* cited by examiner

*Primary Examiner* — Javier G Blanco
(74) *Attorney, Agent, or Firm* — Offit Kurman; Gregory A. Grissett; Chad Sayala

(57)                ABSTRACT

A system and method for fusing the sacroiliac joint is described herein. The system includes a first sacrum anchor and a first compression anchor for implantation through a bore in the iliac bone into engagement with the first sacrum anchor. The first sacrum anchor includes an external thread portion, and an internal channel defined by an inner surface. The inner surface includes an internal thread portion. The first compression anchor includes an outer thread portion along part of the shaft configured to engage the internal thread portion of the first sacrum anchor. Rotation of the first compression anchor draws the first compression anchor toward the first sacrum anchor when the outer thread portion of the first compression anchor is threadably engaged with the internal thread portion of the first sacrum anchor. This configuration allows a user to dial in the appropriate compression on the SI joint.

17 Claims, 15 Drawing Sheets

BONE FIXATION SYSTEM FOR SACROILIAC JOINT AND RELATED METHODS

CROSS-REFERENCE TO RELATED APPLICATIONS

The present application claims priority to and the benefit of U.S. Provisional Patent Application No. 63/323,301, filed Mar. 24, 2022, entitled "BONE FIXATION SYSTEM FOR OF SACROILIAC JOINT AND RELATED METHODS", the entire contents of this application is herein incorporated by reference into the application for all purposes.

TECHNICAL FIELD

The present disclosure relates to a bone fixation system for of sacroiliac joint and related methods.

BACKGROUND

Sacroiliac ("SI") joints are susceptible to injury and degeneration due to the large amount of stress put upon them from the upper body. Acute and chronic injury, degeneration, and laxity of the supporting ligaments of the SI joint can result in low back and radiating buttock and leg pain in afflicted patients. Stabilization or immobilization (fixation) of the SI joint is commonly advocated as a surgical treatment for many SI joint disorders. Existing procedures to stabilize and immobilize the SI joint, however, may result in significant trauma to the major nerves, blood vessels, and muscle groups of the back and hip. In addition, compression between the sacrum and iliac bones cannot be altered during these procedures.

SUMMARY

An embodiment of the present disclosure is a bone fixation system for compression of a sacroiliac joint defined between a sacrum and an iliac bone. The bone fixation system includes a first sacrum anchor that extends along a first central axis. The first sacrum anchor includes a first proximal end, a first distal end spaced from the first proximal end along the first central axis, an external thread portion, and an internal channel defined by an inner surface. The inner surface including an internal thread portion within the internal channel opposite the external thread portion. An entirety of the external thread portion is aligned with the internal thread portion along a radial direction that is perpendicular to the first central axis. The bone fixation system further includes a first compression anchor for implantation through a bore in the iliac bone into engagement with the first sacrum anchor. The first compression anchor includes a head, a shaft that is elongate along a second central axis and that extends relative to the head, and an outer thread portion along part of the shaft. The outer thread portion is configured to engage the internal thread portion of the first sacrum anchor. Rotation of the first compression anchor about the second central axis draws the head of the first compression anchor toward the first sacrum anchor when the outer thread portion of the first compression anchor is threadably engaged with the internal thread portion of the first sacrum anchor.

Another embodiment of the present disclosure is a guidance assembly configured to guide one or more anchors toward a target location at or near a sacroiliac joint. The guidance assembly includes a working cannula that is elongate along an insertion axis, the working cannula having a proximal end, a distal end spaced from the proximal end along the insertion axis, and a channel that extends from the proximal end toward the distal end along the insertion axis. The guidance assembly further includes an outrigger having an insertion arm that extends along a first direction. The guidance assembly further includes a lateral arm that extends along a second direction that is perpendicular to the first direction. The guidance assembly further includes a guide arm coupled to the lateral arm and spaced from the insertion arm along the second direction. The insertion arm is insertable into the channel along the insertion axis so as to inhibit the lateral movement of the outrigger relative to the working cannula along a lateral direction that is perpendicular to the insertion axis when the outrigger is inserted into the working cannula. The guide arm defines that first hole and a second hole configured to receive therethrough a first anchor system and a second anchor system, respectively.

Another embodiment of the present disclosure is a method for fixing an iliac bone with respect to a sacrum across a sacroiliac joint defined between the sacrum and the iliac bone. The method includes delivering an implant into the sacroiliac joint along an inferior insertion axis that extends at least partially along an inferior-superior direction, wherein the inferior-superior direction is perpendicular to a posterior-anterior direction. The method further includes advancing a first sacrum anchor in a lateral direction across the sacroiliac joint to a first location in the sacrum, wherein the lateral direction is perpendicular to the posterior-anterior direction. The method further includes threadably engaging an external thread portion of the first sacrum anchor with the sacrum until a proximal end of the first sacrum anchor is substantially aligned with a surface of the sacrum. The method further includes advancing a first compression anchor through a first bore in the iliac bone and across the sacroiliac joint so that a) an outer thread portion on a shaft of the first compression anchor engages an internal thread portion of the first sacrum anchor and b) a head of the first compression anchor abuts a surface of the iliac bone. The method further includes applying torque to the head of the first compression anchor to cause the head of the first compression anchor and the iliac bone to move closer to or further away from the proximal end of the first sacrum anchor.

BRIEF DESCRIPTION OF THE DRAWINGS

The foregoing summary, as well as the following detailed description of illustrative embodiments of the present application, will be better understood when read in conjunction with the appended drawings. For the purposes of illustrating the present application, there is shown in the drawings illustrative embodiments of the disclosure. It should be understood, however, that the application is not limited to the precise arrangements and instrumentalities shown. In the drawings.

DETAILED DESCRIPTION OF ILLUSTRATIVE EMBODIMENTS

Embodiments of the present disclosure include a bone fixation system 10 configured to stabilize and/or immobilize the sacroiliac ("SI") joint J. The SI joint J is typically referred to as the space between the sacrum S and the iliac bone I (FIGS. 7-10, 17-20). The bone fixation system 10 may include one or more anchor systems 20 and an optional implant 80 (FIGS. 1-10, 17-20). The bone fixation system 10 may be implanted into the SI joint J with aid of various instrumentation including an guidance assembly 110 (FIGS. 11-16) that may be used to guide and position the anchor systems 20 in place in the SI joint J. The bone fixation system 10 may be used to stabilize or immobilize the SI joint J in response to various SI joint disorders. Acute and chronic injury, degeneration, and laxity of supporting ligaments of the SI joint may result in radiating pain in the buttocks or legs or lower back pain. The bone fixation system 10 as described herein may be used to address or mitigate the impact of such disorders.

Figure 1:
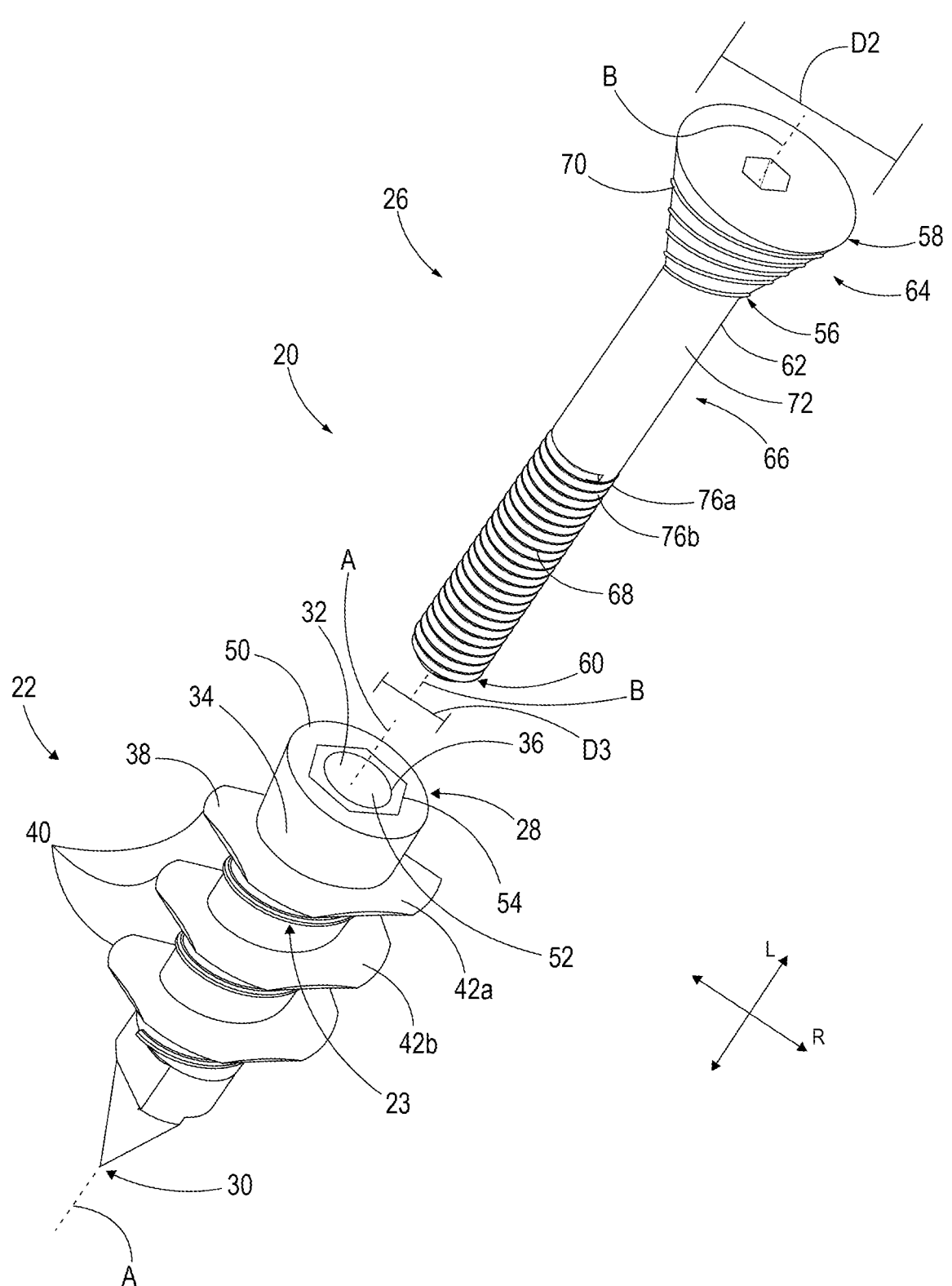
FIG. 1 is a perspective exploded view of an anchor system used in fusing a sacroiliac joint, according to an embodiment of the present disclosure.
Figure 2:
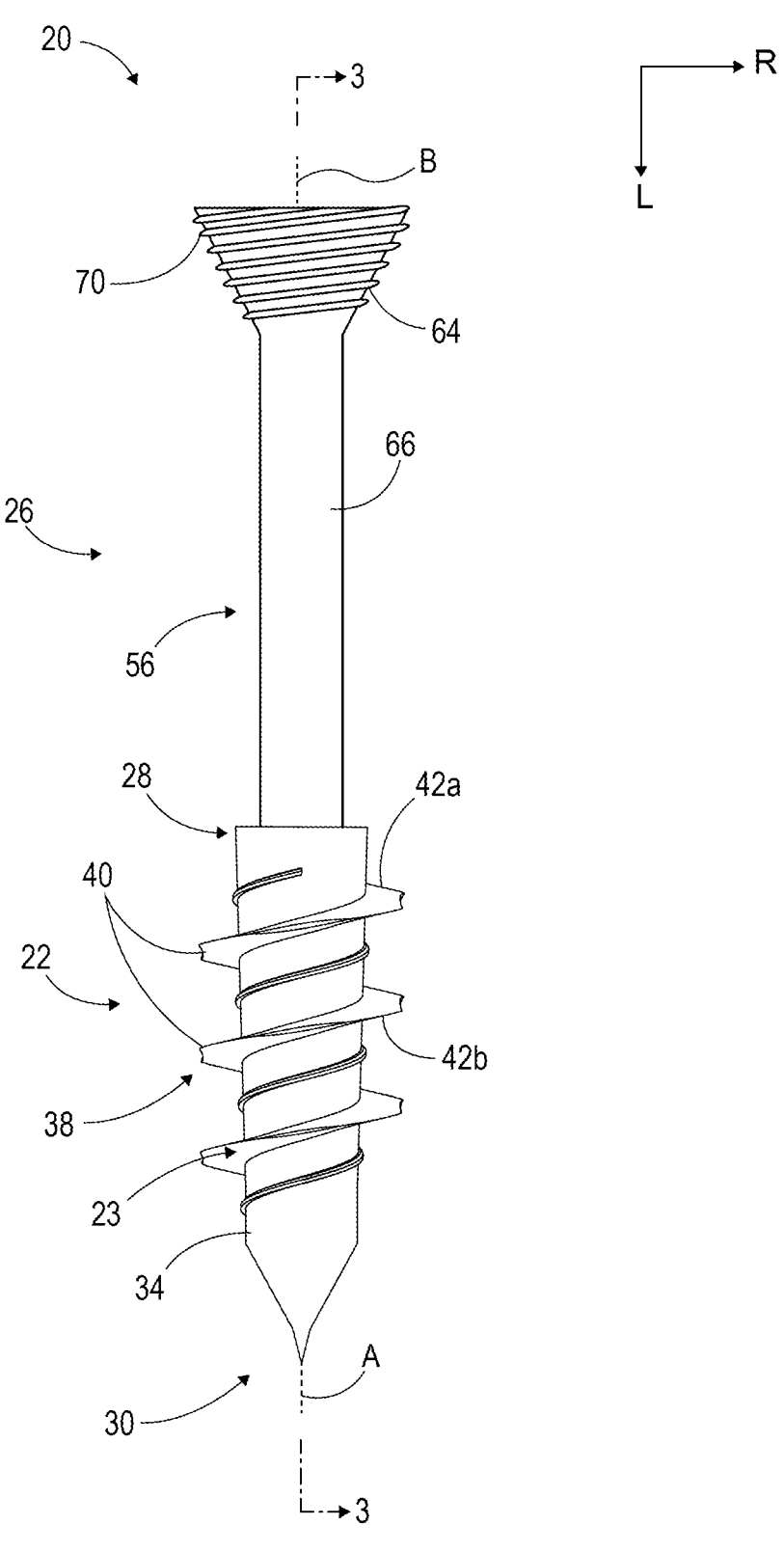
FIG. 2 is a plan view of the anchor system shown in FIG. 1.
Figure 3:
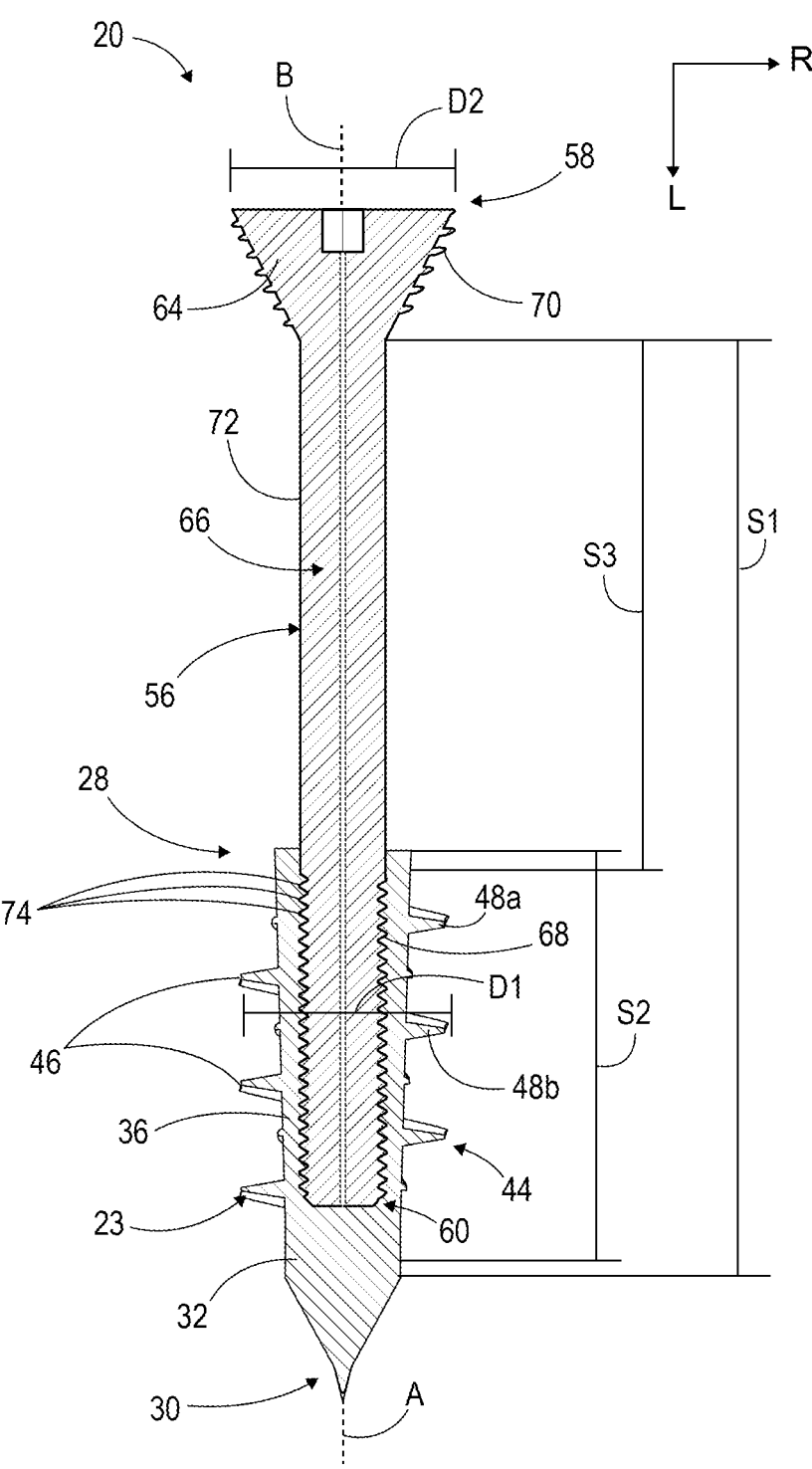
FIG. 3 is a cross-sectional view of the anchor system taken along line 3-3 in FIG. 2.

Referring to FIGS. 1-3, an anchor system 20 may include a sacrum anchor 22 and a compression anchor 26. The sacrum anchor 22 is configured to be secure to the sacrum S (FIGS. 7-10, 17-20) and the compression anchor 26 is configured to engage the iliac bone I and the sacrum anchor 22, as further explained below. The sacrum anchor 22 is elongated along a first central axis A that extends along a longitudinal direction L. The sacrum anchor 22 includes a sacrum anchor body 23 defining a proximal end 28, a distal end 30 spaced from the proximal end 28 along the first central axis A, an inner surface 32, and outer surface 34 spaced from the inner surface 32 along a radial direction R that is perpendicular to the longitudinal direction and central axis A. The sacrum anchor body 23 further includes an internal channel 36 defined by the inner surface 32. The internal channel 36 extends from the proximal end 28 toward the distal end 30 along the first central axis A. The sacrum anchor 22 also includes a first cannulation 27 that extends distal end 30 toward the proximal end. The cannulation 27 is located in the portion of the shaft that does not threadably engage with the compression anchor 26. The proximal end 28 may engage a driving instrument. The distal end 30 defines a point and may include reverse cutting flutes to facilitate engagement with the bone.

As shown in FIG. 1, the proximal end 28 of the sacrum anchor is configured to engage one or more driving instruments. For instance, the proximal end 28 may define a proximal surface 50 that is generally perpendicular to central axis A, and an engagement element 52 that extends into the sacrum anchor 22 along the central axis toward the distal end 30 of the anchor. The engagement element 52 may include one more linear walls 54 that define a surface to receive torque from a driving instrument and transfer that torque into rotation of the sacrum anchor 22. The engagement element may be hexagonal, star-shaped, plus-shaped, or have any configuration suitable for such receiving and transferring torque into rotation of the sacrum anchor 22. The engagement element 52 is shown proximal to internal channel such that the compression anchor 26 can engage the internal channel 36 without contacting the engagement element 52. In addition, the engagement element 52 is recessed into the sacrum anchor 22 with its linear walls facing the central axis. However, engagement element 52 could project proximally with respect to the proximal surface 50 such that its linear walls 54 face outwardly.

The sacrum anchor 22 includes external threads and internal threads to engage the sacral bone S and the compression anchor 26, respectively. As illustrated, the outer surface 34 defines an external thread portion 38 that is configured to engage the sacrum S. The external thread portion 38 includes a plurality of external thread peaks 40, such as a first peak 42a and a second peak 42b. The external thread portion 38 defines a first pitch that extends between the first peak 42a and the second peak 42b. In addition, as illustrated, the external thread portion 38 may define a buttress type thread. However, other types of threads may be used as needed.

In accordance with the embodiment illustrated in FIGS. 1-3, the external thread portion 38 may define a maximum external diameter D1 that is perpendicular to the first central axis A. The maximum external diameter D1 is extends from and between the outermost peaks of the external thread peaks 40 that is also perpendicular to the first central axis A. In such an example, the maximum external diameter D1 is between about 5.0 mm and about 20.0 mm. However, the maximum external diameter D1 is not limited to 5 mm to 20 mm.

Continuing with FIGS. 1-3, the inner surface 32 of the sacrum anchor 22 includes an internal thread portion 44 that is generally opposite the external thread portion 38. The internal thread portion 44 includes a plurality of internal thread peaks 46, such as a first peak 48a and a second peak 48b. The internal thread portion 44 defines a second pitch that extends between the first peak 48a and the second peak 48b. In the illustrated embodiment, the first pitch of the external thread peaks 40 is greater than the second pitch of the internal thread peaks 46. Thus, in one example, the internal and external thread patterns are dissimilar. However, the internal thread portion 44 may include any particular type of thread as needed. In accordance with the embodiment illustrated in FIGS. 1-3, an entirety of the external thread portion 38 is aligned with an entirety of the internal thread portion 44 along a radial direction R that is perpendicular to the first central axis A. In alternative embodiments, however, the external thread portion 38 and the internal thread portion 44 may not align or be coextensive with respect to each other. The cannulation 27 extends from the distal-most end of the internal thread portion 44 to the distal end 30 of the anchor 22. The cannulation allows the anchor to slide over a guidewire.

The internal thread portion 44 may also extend along a first length L1 of the inner surface 32. The first length L1 in this case extends from a proximal-most internal thread peak to a distal-most internal thread peak along and parallel to the central axis A (FIG. 3). In one example, the first length L1 is between about 5 mm and 20 mm. In another example, the first length L1 is between about 7.5 mm and 15 mm. In yet another example, the first length L1 is about 10 mm. The extent of the first length L1 may be used to adjust the extent of compression of the iliac bone I toward the sacrum S at the SI joint J as discussed further below. In any event, the internal thread portion 44 is configured and fixed to engage the compression anchor 26 as will be further explained below while the external thread portion 38 is sized and configured to engage cortical and cancellous bone in the sacrum 8 in such way that once implanted, the sacrum anchor is substantially fixed in place.

Continuing with FIGS. 1-3, the compression anchor 26 is configured to engage the sacrum anchor 22 and the iliac bone I. The compression anchor 26 is elongated along a second central axis B that extends along a longitudinal direction L. The compression anchor includes a compression anchor body 56 defining a proximal end 58, a distal end 60 spaced from the proximal end 58 along the second central axis B, and an outer surface 62. The compression anchor body 56 may include a head 64 at the proximal end 58, a shaft 66 that extends relative to the head 64 along the central axis B, and an outer thread portion 68 that extends along part of the shaft 66. The proximal end 58 may engage bone and the outer thread portion 68 is configured to engage the internal thread portion 44 of the sacrum anchor 22. The compression anchor includes a second cannulation 69 that extends from the head 64 to a distal end 60 of the shaft 66. When the compression anchor 26 is threadably engaged with the sacrum anchor 22, the first cannulation 27 of the sacrum anchor is substantially aligned with the second cannulation 69 along axis B.

Continuing with FIGS. 1-3, the head 64 of the compression anchor 26 is sized to engage a surface of the iliac bone and compress the iliac bone I toward the sacrum S when the compression anchor 26 engages the sacrum anchor 22. In such an example, the head 64 is generally larger in a cross-sectional dimension than the shaft 66. As illustrated, the head 64 may define a maximum outer head diameter D2 that is perpendicular to the central axis B. Furthermore, the head 64 may include outer head threads 70 configured to engage the bone as needed. The maximum outer head diameter D2 extends from and between two opposite and outermost points of the head and intersects and is perpendicular to the central axis B. In one example, the maximum outer head diameter may be between 5 mm and 20 mm. In another example, the maximum outer head diameter may be between 7.5 mm and 15 mm. In yet another example, the maximum outer head diameter may be about 10 mm.

The shaft 66 of the first compression anchor 26A defines the distal end 60 and includes a shaft length S1 that extends from the head 64 to the distal end 60 along the second central axis B. The shaft 66 also defines a maximum shaft diameter D3 that is perpendicular to the central axis B. The maximum shaft head diameter D3 extends from and between two opposite and outermost points of the shaft and intersects and is perpendicular to the central axis B. As illustrated, the outer head diameter is at least about 1.25 times the maximum shaft diameter. In addition, in some instances, the outer head diameter of the compression anchor 26 may generally correspond to, and is substantially similar to, the maximum external diameter of the sacrum anchor 22.

As illustrated, the shaft 66 includes the outer thread portion 68 and a smooth surface 72. The smooth surface 72 extends from the head 64 to a proximal most edge of the outer thread portion 68. The smooth surface length S3 may range between 5 and 20 mm. In one example, the smooth surface length S3 ranges between 7.5 and 15 mm. In yet another example, the smooth surface length S3 may be about 10 mm. The length of the smooth surface is not limited to these values. Furthermore, in alternative embodiments, the entirety of the shaft may be threaded.

The outer thread portion 68 is configured to engage the internal threads of the sacrum anchor 22. Accordingly, the outer thread portion 68 includes a plurality of outer thread peaks 74, such as a first peak 76a and a second peak 76b. The compression anchor 26 defines a pitch (e.g. a third pitch) that extends between the first peak 76a and the second peak 76b. In the illustrated embodiment, the pitch of the outer thread peaks 74 is similar to the second pitch of the internal thread peaks 46 on the sacrum anchor 22 to facilitate threadable engagement therewith.

The outer thread portion 68 extends along a part of the shaft 66. As illustrated, the outer thread portion 68 has an outer thread length S2 that extends from a proximal-most outer thread peak to a distal-most outer thread peak along and parallel to the central axis B (FIG. 3). The outer thread length S2 is no greater than about one-half of the total shaft length S1. In one example, the outer thread length S2 is between about 5 mm and 20 mm. In another example, the outer thread length S2 is between about 7.5 mm and 15 mm. In yet another example, the outer thread length S2 is about 10 mm. The length of the outer thread portion 68 may vary as needed. In one example the outer thread length S2 of the compression anchor 26 is substantially similar to the internal thread length L1 of the sacrum anchor. However, the outer thread length S2 and internal thread length L1 may vary as needed.

In use, the sets of anchors are used to help control compression of reduction of the SI joint J. For example, once the sacrum anchor 22 is implanted into a bore in the sacrum S, the compression anchor 26 may be advanced through a bore in the iliac bone into threadable engagement with sacrum anchor 22. Specifically, in such a situation, outer thread portion 68 engages the internal thread portion 44 of the sacrum anchor while the head 64 locks into the iliac bone proximate its lateral surface. In this configuration, the central axis A of the sacrum anchor 22 and the central axis B of the compression anchor 26 are coaxial. Furthermore, rotation of the compression anchor 26 about the second central axis B in a first rotational direction draws the head 64 of the compression anchor 26 toward the sacrum anchor 22. And rotation of the compression anchor 26 about the second central axis B in a second rotational direction opposite the first rotational direction can cause the head 64 of the compression anchor 26 to move away the sacrum anchor 22. As will be explained below, this can be used selectively "dial in" the appropriate compression on the SI joint J without causing damage to the sacrum bone or causing the sacrum anchor 22 to extend too far into the sacrum bone.

Figure 4:
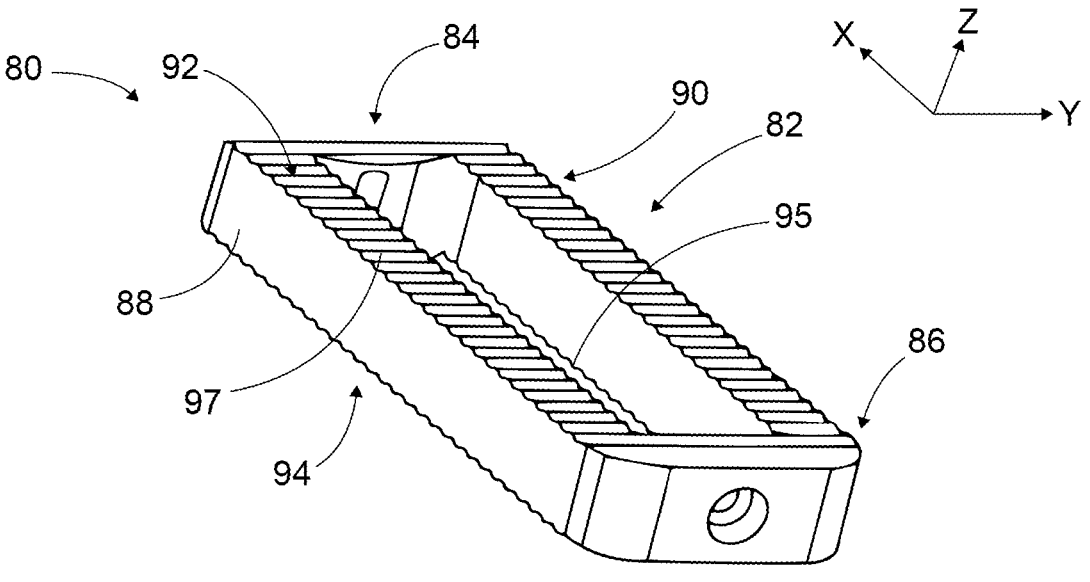
FIG. 4 is a perspective view an implant for placement in the sacroiliac joint, according to an embodiment of the present disclosure.
Figure 5:
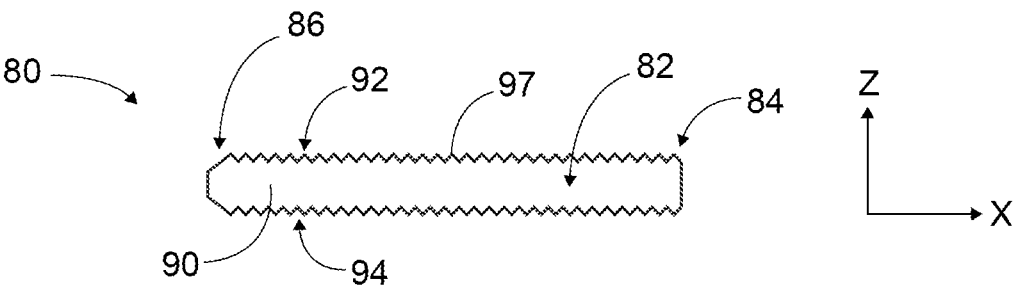
FIG. 5 is a side view of the implant shown in FIG. 4.
Figure 6:
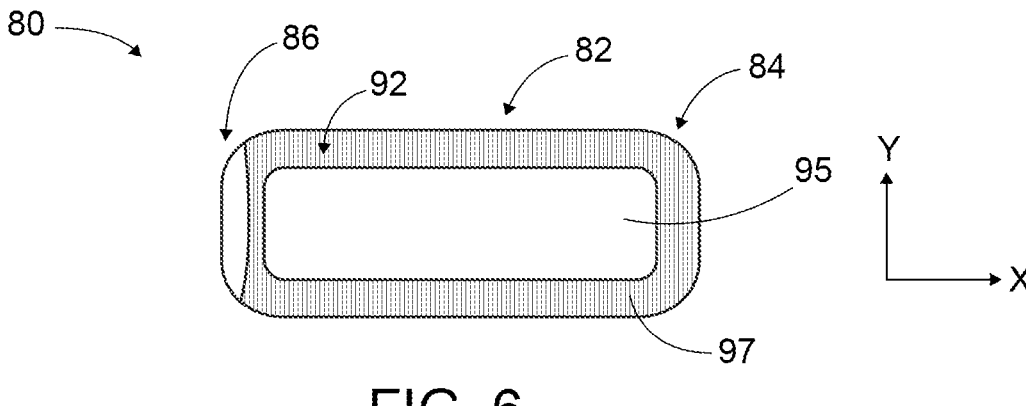
FIG. 6 is a top plan view of the implant shown in FIG. 4.

Referring now to FIGS. 4-6, the bone fixation system 10 may include an optional implant 80 configured to be placed in the SI joint J. The implant 80 may include a body 82 having a first end 84, a second end 86 spaced from the first end along an implant along a length axis X, a first side 88, and a second side 90 opposite the first side 88 along a width axis Y, a first contact surface 92 and a second contact surface 94 opposite the first contact surface 92 along a transverse axis Z. The long axis X, width axis Y, and transverse axis Z are perpendicular to each other and intersect each other. Thus, the implant 80 is shown as being generally elongate along the long axis X and may include one or more engagement features 96 for coupling to an instrument during placement of the implant in the SI joint. The implant 80 may have one or more apertures 95 that extends through its body 82. As illustrated, the aperture 95 extends from the first contact surface 92 to the second contact surface 94. However, the aperture 95 could also extend through the sides 88, 90 or the ends 84, 86. While one aperture 95 is shown, the implant can have more than one aperture. The apertures may be used to facilitate bone in-growth or may be filled with a graft material or other material prior to implantation.

In the illustrated embodiment, the first and second contact surfaces include gripping ridges 97, designed to engage bone. In alternative embodiments, however, the gripping ridges 97 may be disposed along the first end 84, second end 86, first side 88, or second side 90.

The implant 80 may include one or more anchor bores (not shown) that receive anchors as needed. For instance, in some cases, the implant 80 may be positioned in the joint space and one or more anchors may be used to secure the implant 80 in place via the anchor bores. However, the implant 80 may be placed in the joint space and the sets of anchors as described herein may be positioned proximate to the implant 80.

The implant 80 may be formed from any biocompatible material, including polymeric materials, such as PEEK, titanium, graft materials, or combinations thereof. The implant 80 may be a monolithic part, such as monolithic spacer. Alternatively, the implant 80 may comprise one or more implant components.

Figure 7:
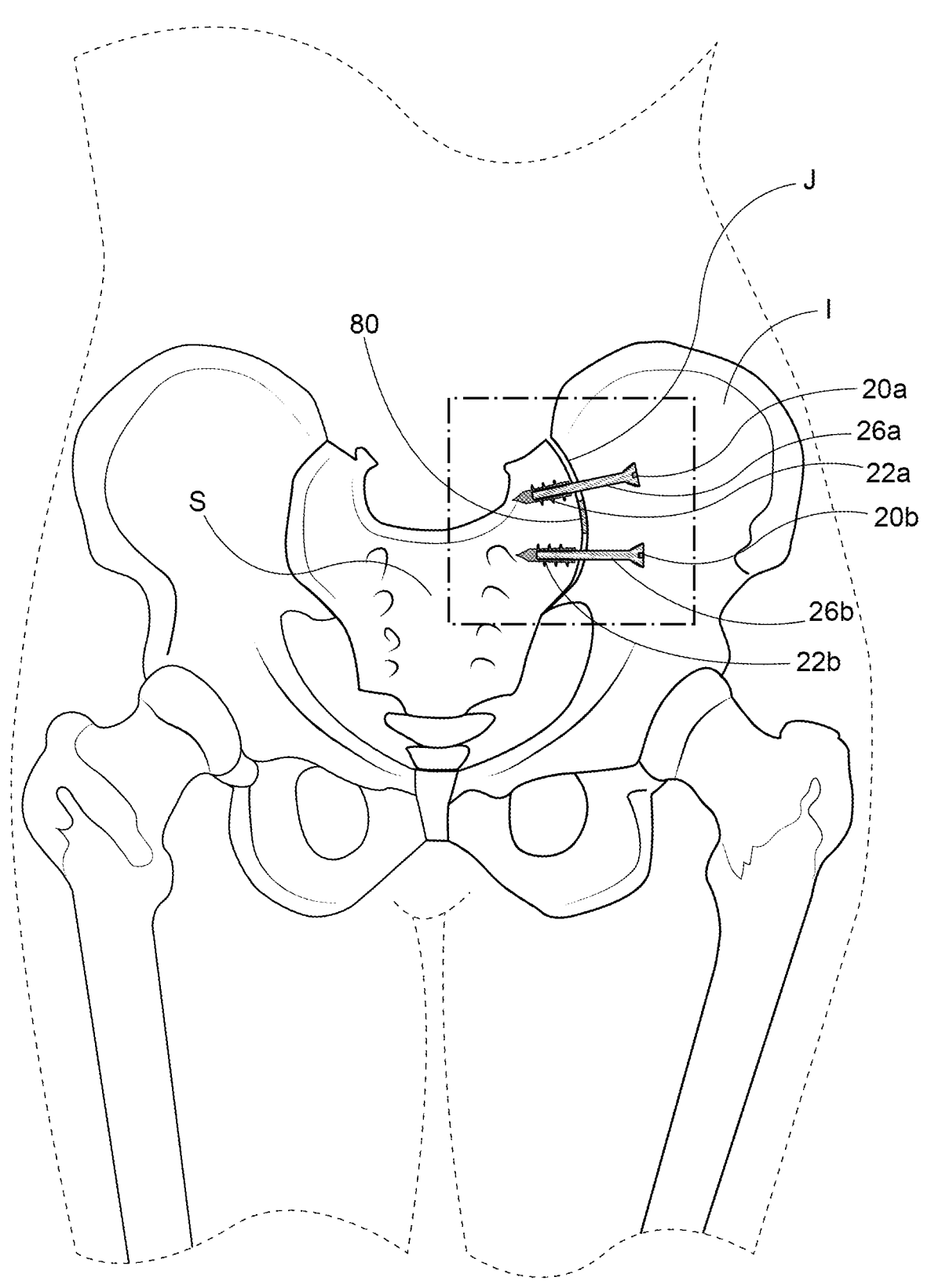
FIG. 7 is a schematic anterior view showing a partial section of the anchor system shown in FIG. 1 secured across the sacroiliac joint.
Figure 8:
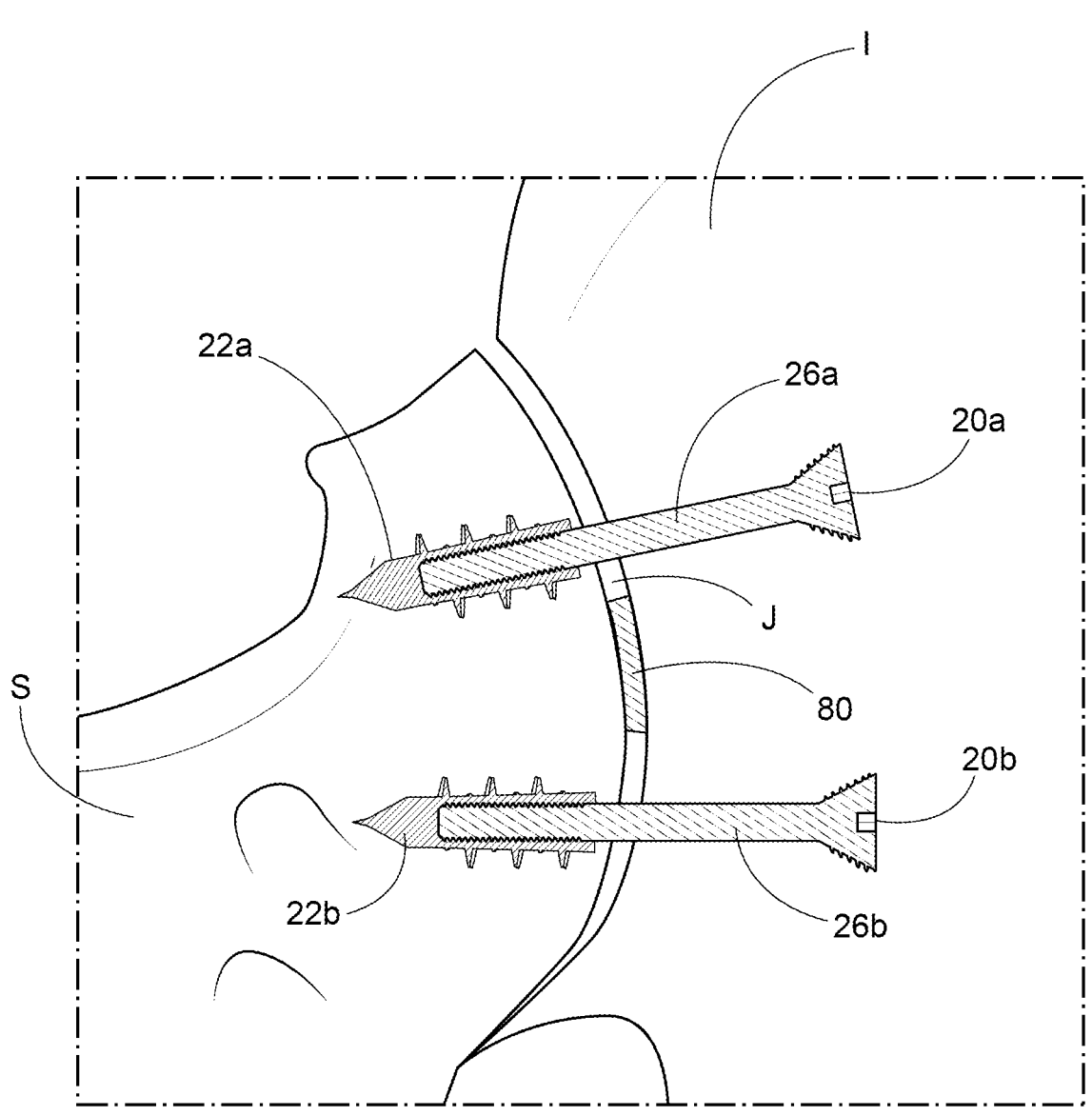
FIG. 8 is a detailed sectional view of part of FIG. 7.

In typical implementations, the bone fixation system 10 may include at least two anchor systems 20 implanted in the SI joint J, as shown in FIGS. 7-10. For example, the bone fixation system 10 may include a first anchor system 20A and a second anchor system 20B implanted in the sacrum and the iliac bone as shown in FIGS. 7 and 8. Furthermore, the first anchor system 20A may include a first sacrum anchor 22A and a first compression anchor 26A and the second anchor system 20B may include a second sacrum anchor 22B and a second compression anchor 26B, etc. Accordingly, references numbers 20, 20A and 20B may be used interchangeably to refer to any particular anchor system. Likewise, the reference numbers 22, 22A, and 22B may be used interchangeably to refer to a sacrum anchor and each may have common features. The reference numbers 26, 26A, and 26B may be used interchangeably to refer to a compression anchor and each may have common features. Therefore, unless stated otherwise, the first sacrum anchor of the first anchor system may have features and elements that are common with the second sacrum anchor of the second anchor system. In describing embodiments of the present disclosure in this document, we refer generally to the sacrum anchor and the compression anchor. It is apparent, however, the sacrum anchor can refer to a first sacrum anchor, a second sacrum anchor, etc. In addition, it also is apparent, however, the compression anchor can refer to a first compression anchor, a second compression anchor, etc. Furthermore, in some instances an anchor system may be differing sets of anchors as needed.

Figure 9:
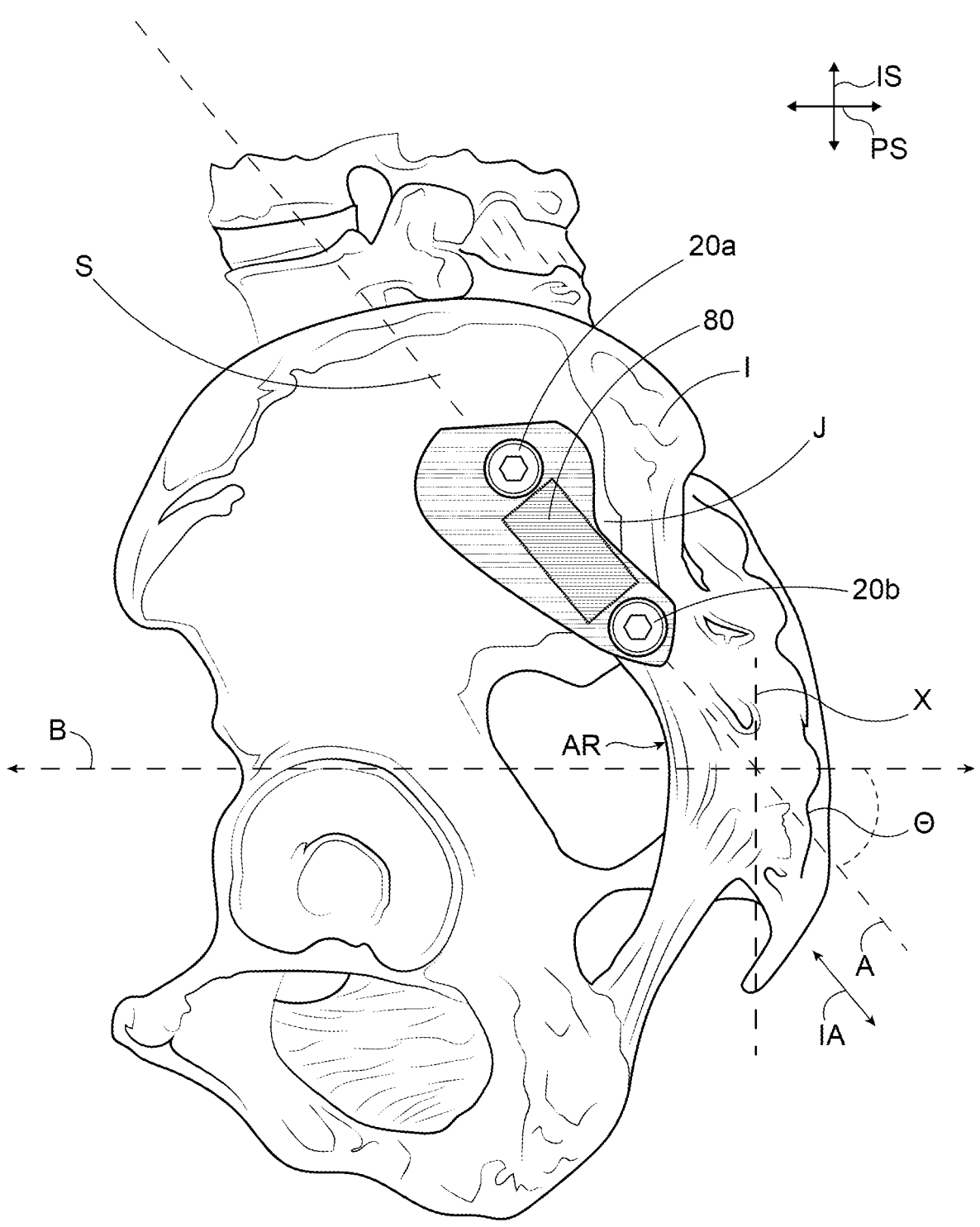
FIG. 9 is a schematic lateral view of the anchor system and implant disposed in the sacroiliac joint, according to an embodiment of the present disclosure.
Figure 10:
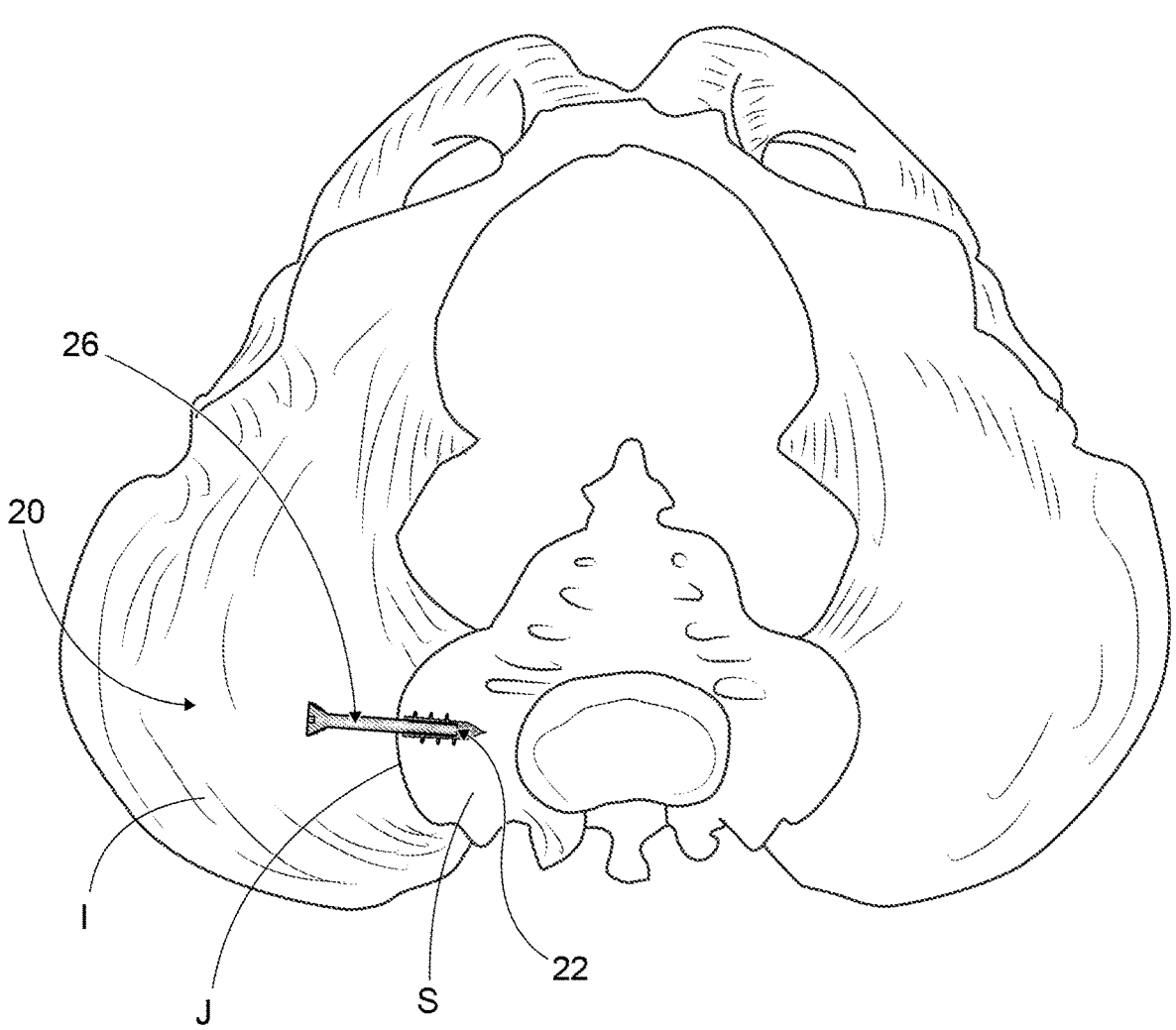
FIG. 10 is a schematic inferior view of the anchor system and implant disposed in the sacroiliac joint, according to an embodiment of the present disclosure.
Figure 11:
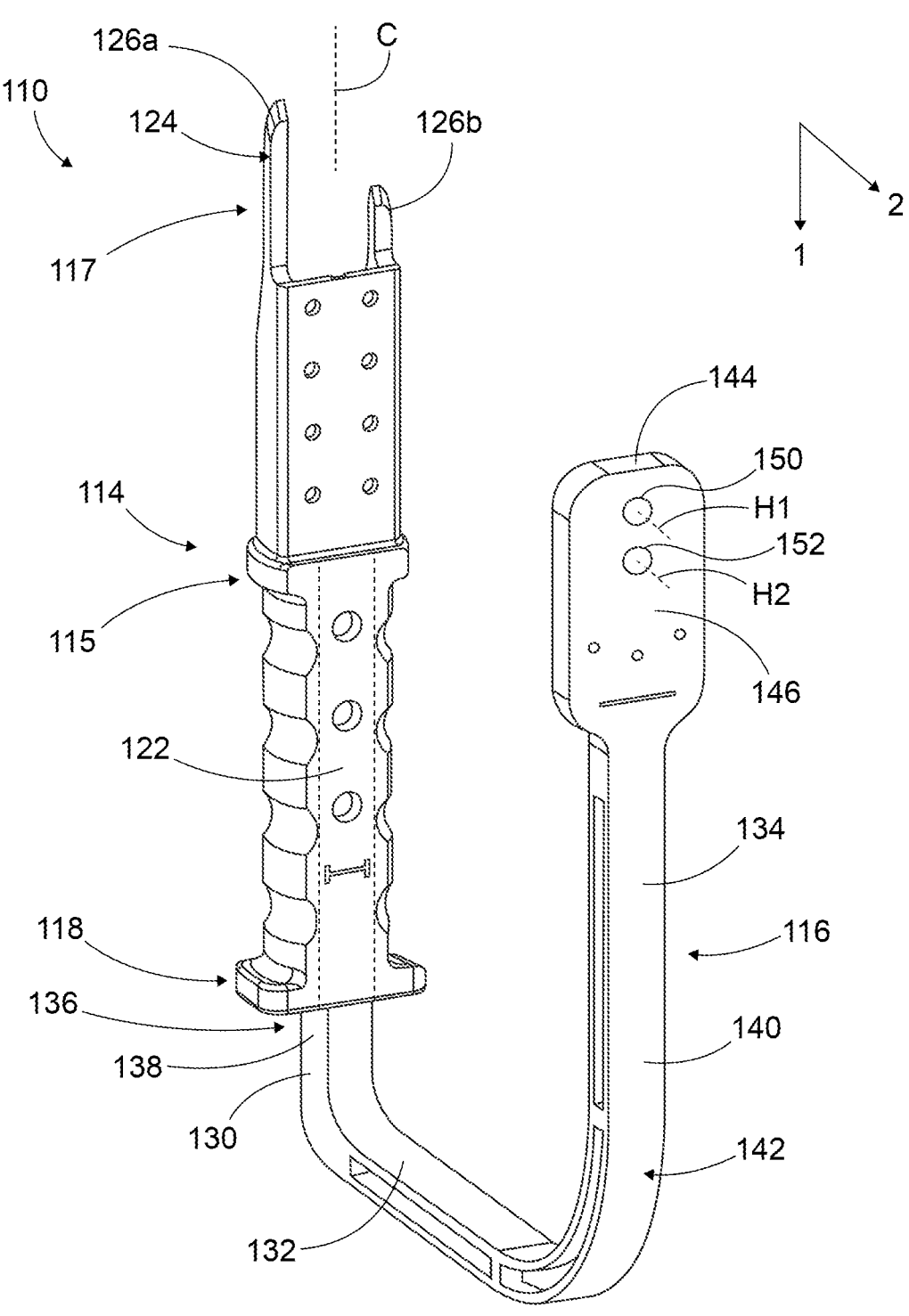
FIG. 11 is a perspective view of a guidance assembly, according to an embodiment of the present disclosure.
Figure 12:
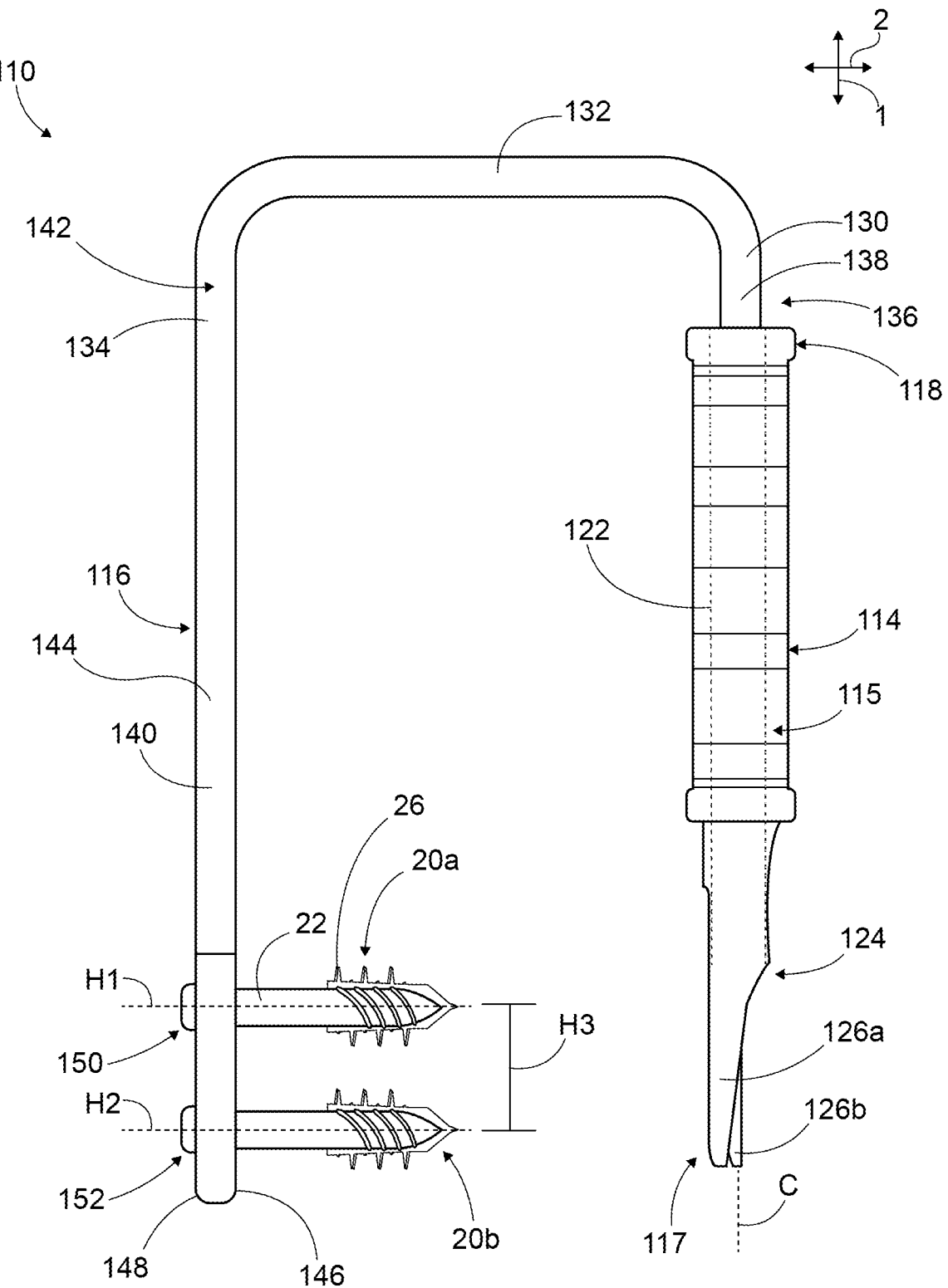
FIG. 12 is a plan view of the guidance assembly shown in FIG. 11.

Referring now to FIGS. 11-16, the bone fixation system 10 may include one or more instruments to prepare the joint space, facilitate implantation of the anchor system 20 and implant 80, and permit the user to tune the anchor system to the appropriate compression level for the SI joint J. Typically, the anchor system 20 is inserted via a lateral approach using a guidance assembly 110 as illustrated in FIGS. 11 and 12. More specifically, the guidance assembly 110 is configured to guide one or more anchors toward a target location at or near a sacroiliac joint J. The guidance assembly 110 may include a working cannula 114 and an improved outrigger 116. The working cannula 114 may be used to guide other sets of instruments or tools to prepare the joint space and insert an implant 80 via an inferior approach. The inferior approach as defined herein is best shown in FIG. 9. The inferior approach is delivering an implant 80 through an inferior access region AR into the sacroiliac joint J in inferior-access direction IA. The inferior-access direction IR is non-orthogonal to an inferior-superior direction IS and a posterior-anterior direction PS. In this regard, the inferior-superior direction IS is substantially perpendicular to the posterior-anterior direction PA. The inferior access direction IA is generally, therefore, the direction toward the inferior access region AR, which is generally on the inferior side of the SI joint. The inferior access direction IA may extend along an axis A that defines an angle θ of between 5 degree and 40 degrees with respect to an axis B that extends in the posterior-anterior direction PA. The intersection of axes A and B, which define the angle θ, lies on a plane X. The plane X is 1) parallel to the inferior-superior direction IA, 2) parallel to the sagittal plane (not shown), 3) is anterior to coccyx (not numbered), 4) posterior to the ischium (not numbered), and is perpendicular the axis B. Angle θ thus is defined an lies on the posterior side of the plane X. In certain alternative embodiments, however, the working cannula 114 may be used to guide instruments and the implant 80 via a posterior approach.

The working cannula 114 is configured to be positioned adjacent to a target location of the SI joint J (FIGS. 7-10, 17-20). As shown, the working cannula 114 is elongate along an insertion axis C and includes a cannula body 115. The cannula body 115 may define a proximal end 118, a distal end 117 spaced from the proximal end 118 along the insertion axis C, and a guide channel 122 that extends from the proximal end 118 toward the distal end 117 along the insertion axis C. The body 115 of the working cannula 114 further includes an inner surface 120 that at least partially defines the guide channel 122.

Figure 13:
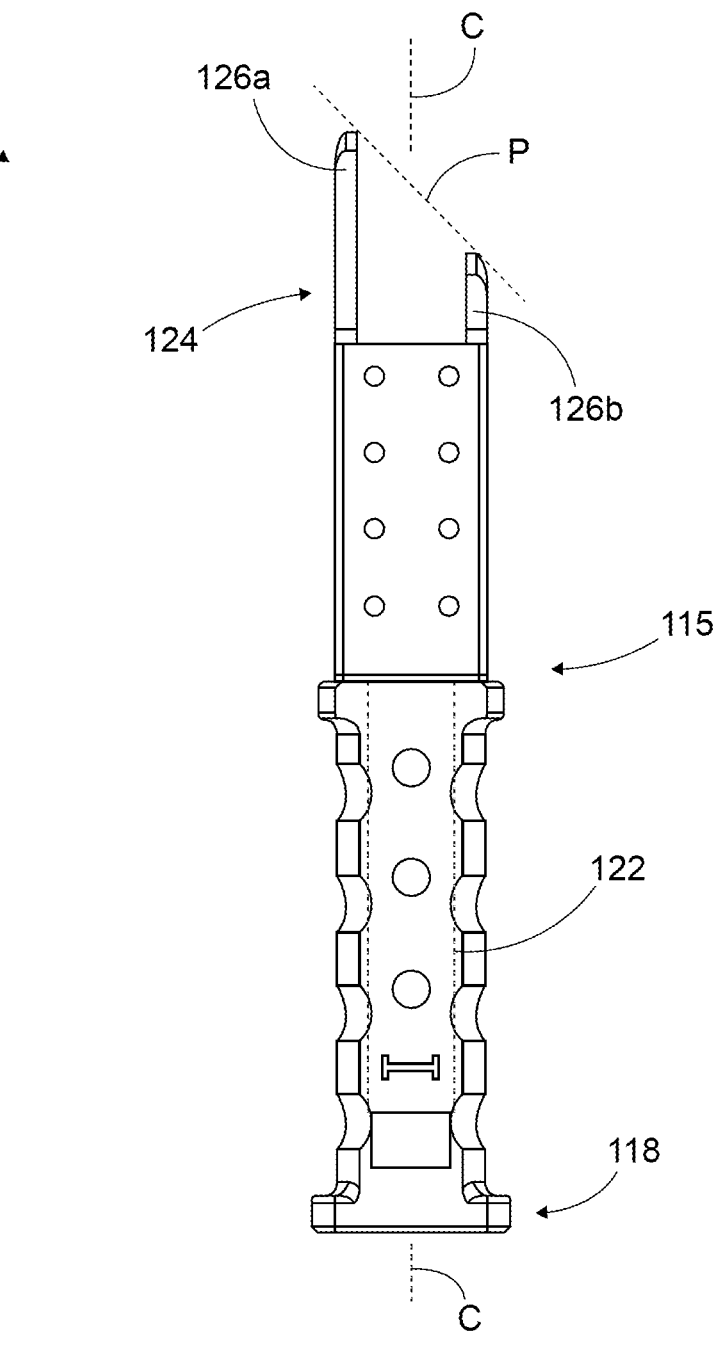
FIG. 13 is a side view of a working cannula of the guidance assembly shown in FIG. 11, according to an embodiment of the present disclosure.
Figure 14:
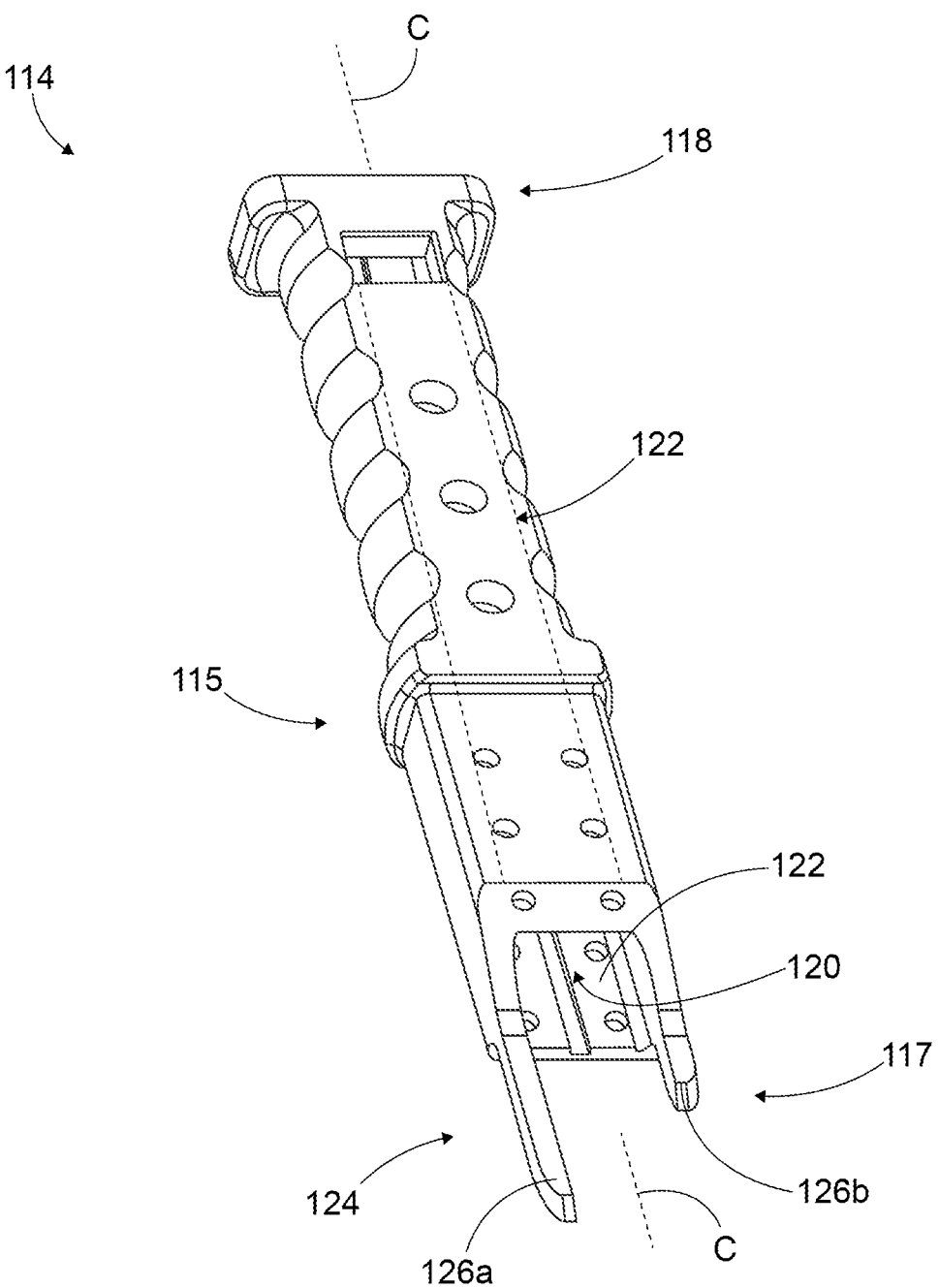
FIG. 14 is a perspective view of the working cannula shown in FIG. 13.

As shown in FIGS. 13 and 14, the distal end 117 of the working cannula includes one or more placement elements 124 sized and configured to orient the working cannula relative the SI joint when the placement elements 124 are in contact with the target location. Placement elements 124 are sized and configured to orient the working cannula substantially along an inferior insertion direction IA, which is aligned with inferior access region IR. In this manner, instruments, implant 80, and other devices, may be inserted through the inferior access region IR, or inferior aspect, of the SI joint J. In accordance with the embodiment as shown in FIGS. 13 and 14, the placement elements 124 may include a first tine 126a and a second tine 126b positioned and sized relative to each other to orient the working cannula 114 at the target location. For instance, the first tine 126a may have a first tine length and the second tine 126b may have a second tine length that is less than the first tine length. This difference in tine length creates a placement plane P that is offset with respect to insertion axis C. It should be appreciated that the first and second tines are illustrative only. A placement element 124 may include any surface shape, projection, curve, or element on the working cannula 114 that can orient the working cannula 114 in the desired insertion trajectory. In use, when tines are on in contact with target location, the placement plane P is basically coplanar with the target location. When in contact with the target location, the working cannula 114, and its insertion axis C, is angularly offset but aligned with inferior insertion direction. In alternative embodiments, however, the placement elements 124 may be not define such an angled placement plane P such that working cannula 114 is not offset with respect to the anatomy to which is in contact with, such as for posterior approach.

Figure 15:
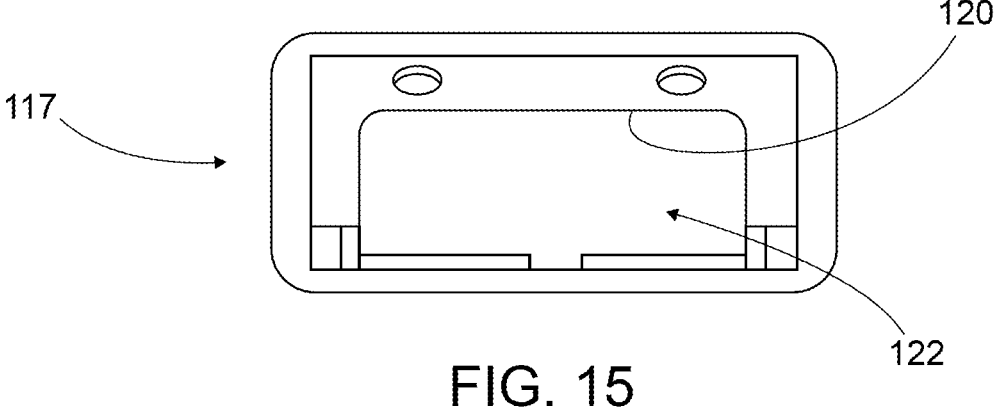
FIG. 15 is an end view of the working cannula shown in FIG. 13.
Figure 16:
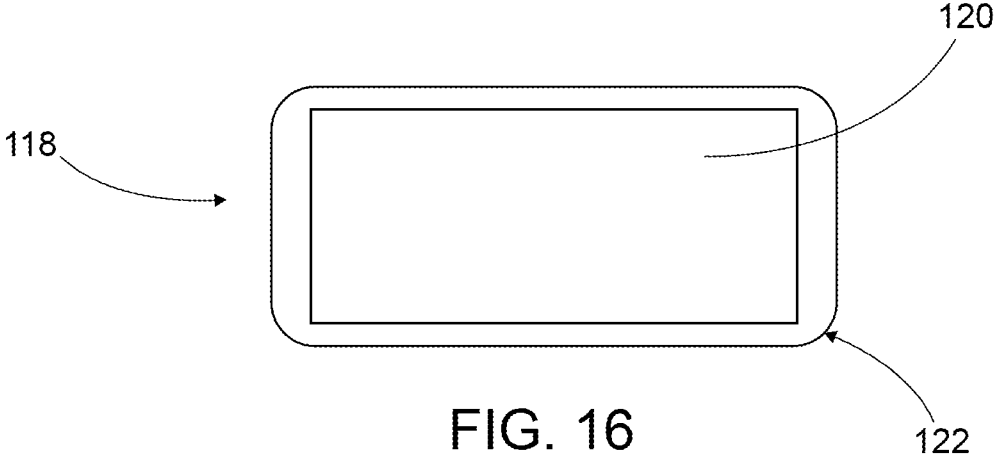
FIG. 16 is another end view of the working cannula shown in FIG. 13.

As shown in FIGS. 15 and 16, the working cannula 114 includes a guide channel 122 that is configured to mate with the outrigger 116. At least the proximal end 118, and the inner surface 120 thereof in particular, defines a first cross-sectional shape of the channel 122. The first cross-sectional shape can be any shape that mates with the outrigger 116 and limits relative lateral and transverse movement between the outrigger 116 and the working cannula 114. In one example, the first cross-section shape is non-circular. In another example, a boundary of the channel 122 has at least a linear component. As illustrated, the first cross-sectional shape is rectilinear.

As shown in FIGS. 11 and 12, the outrigger 116 is configured to facilitate insertion of the anchor systems 20 into the SI joint. The outrigger 116 has an insertion arm 130 that extends along a first direction 1, a lateral arm 132 that extends along a second direction 2 that is perpendicular to the first direction 1, and a guide arm 134 coupled to the lateral arm 132 and spaced from the insertion arm 130 along the second direction 2. The outrigger 116 engages the working cannula 114 and positions the guide arm 134 relative to the target location to facilitate insertion of the anchor systems 20 as described herein.

The insertion arm 130 is insertable into the guide channel 122 along the insertion axis C. The insertion arm 130 defines an insertion end 136 having an external surface 138. The external surface 138, in turn, defines a second cross-sectional shape configured to mate with the first cross-sectional shape of the guide channel 122. The second cross-sectional shape is perpendicular to the first direction 1 and insertion axis C. To be clear, the insertion end 136 can have any shape that mates with the guide channel 122 to limit relative lateral and transverse movement between the outrigger 116 and the working cannula 114. In one example, the second cross-section shape is non-circular. In another example, a boundary of the insertion end 136 has at least a linear component. As illustrated, the second cross-sectional shape is rectilinear and is similar to the first cross-sectional shape of the guide channel 122. Furthermore, the cross-sectional shape of the channel 122, as it extends along the insertion axis, generally slidingly mates with substantially all or a substantial majority of the cross-sectional shape of the outrigger insertion arm 130 along its axis. In other words, in one example, at least 50% of the total surface are of the insertion arm 130 is sliding contact the inner surface 120 of the working cannula 114. In this way, the insertion arm 130 is stable against any significant transverse movement relative to the working cannula 114, but can still easily slide in and out of the guide channel 122 along the insertion axis as needed.

The outrigger 116 has a guide arm 134 that is used to guide the trajectory and insertion of the anchor systems 20 into intended bone. As shown, the guide arm 134 is generally elongate and includes a guide member 140 disposed at its distal end 142. The guide member 140 includes a guide body 144 having a bone-facing surface 146 and trailing surface 148 opposite the bone-facing surface 146 along the second direction 2. The guide body 144 further defines at least a first hole 150 and at least a second hole 152 that are each configured to receive therethrough a first anchor system 20A and a second anchor system 20B, respectively. The first hole 150 extends along a first hole axis H1 and a second hole 152 that extends along a second hole axis H2. As shown, the first hole 150 and the second hole 152 are being oriented such that the first hole axis H1 and second hole axis H2 are generally parallel to the second direction 2. Positioned this way, the first axis H1 and the second axis H2 may intersect target locations where respective anchor systems will be implanted. Furthermore, the first hole 150 and the second hole 152 are spaced apart from each other along the first direction a distance H3 that is typically greater than an overall longitudinal length of an implant (when such an implant is used). The first and second holes 150 and 152 are illustrated as circular openings. It should be appreciated however, that the first and second holes 150, 152 may be elongate slots or include one or more paths to adjust the relative position of the anchor systems as needed during use. In other words, the guide member 140 can be configured to allow a surgeon to adjust the relative distance between the insertion paths of the anchor systems 20A and 20B as needed. Furthermore, the improved stability facilitates use the surgeon in that allows the surgeon to dial in the desired compression of the SI joint J using the directional rotation of the compression anchor relative to the implanted sacrum anchor. Minimizing outrigger play during the procedure minimizes guesswork while also minimizing inadvertent trauma due to over-tightening.

The guidance assembly described herein is a structural and functional improvement of conventional designs use for SI joint fixation. In conventional working cannulas, such as that shown in U.S. Patent App. Pub. No. 2016/0310197 to Black et al., a through-channel in the working cannula that was oriented in a direction that is perpendicular to the insertion axis. That through-channel was used to receive an outrigger. In that design, once the outrigger was inserted in that through-channel, there was significant play and movement of the outrigger both in a direction toward and away from the target site and also in directions transverse to the insertion axis and target side. The design simply failed to provide the desired stability to the outrigger to provide a reliable guide for insertion of the anchors. In the present disclosure, the outrigger 116 is configured to be inserted along the insertion axis C and matingly fits with the working cannular to improve stability of the outrigger 116 and minimize movement of the outrigger in directions that are transverse to the insertion axis C.

Now referring to FIGS. 17-20, a method for utilizing the bone fixation system 10 shown in FIGS. 1-16 will be described. In use, the SI bone fixation system 10 may be used to stabilize or immobilize an SI joint J. Typically, the SI bone fixation system 10 may include a guide wire or guide pin that is inserted into the target location proximate the SI joint J via a delivery device or driving instrument 106. The driving instrument 106 may include a handle end and a driving end. It is possible, though optional, that an implant 80 is delivered to the SI joint J to aid in stabilization. In such an example, the method may include delivering an implant through an inferior access region into the sacroiliac joint in inferior-access direction that is non-orthogonal to an inferior-superior direction and a posterior-anterior direction. In this regard, the inferior-superior direction is substantially perpendicular to the posterior-anterior direction. Additional allograft or other materials may be implanted in the SI joint J proximate the implant.

The guidance assembly 110 may be utilized to facilitate implantation of the anchor system 20. Initially, a user may insert the working cannula 114 through interior access region so that is contacts bones/tissue at or near the SI joint. Then, if needed, an implant, which may be carried by the working cannula 114, in inserted into the joint J. Once the implant is in place a surgeon may insert the outrigger into the working cannula 114. In this regard, the insertion arm 130 is slid into the guide channel 114. The guidance assembly 110 is inserted until the guide member 140 is in position. More specifically, the method may include positioning the guide member 140 with respect to the iliac bone I so that a first hole 150 (or axis H1) in the guide member 140 is aligned with the first location of the sacrum S and the second hole 152 (or axis H2) in the guide member 140 may be aligned with a second location of the sacrum S.

Figure 17:
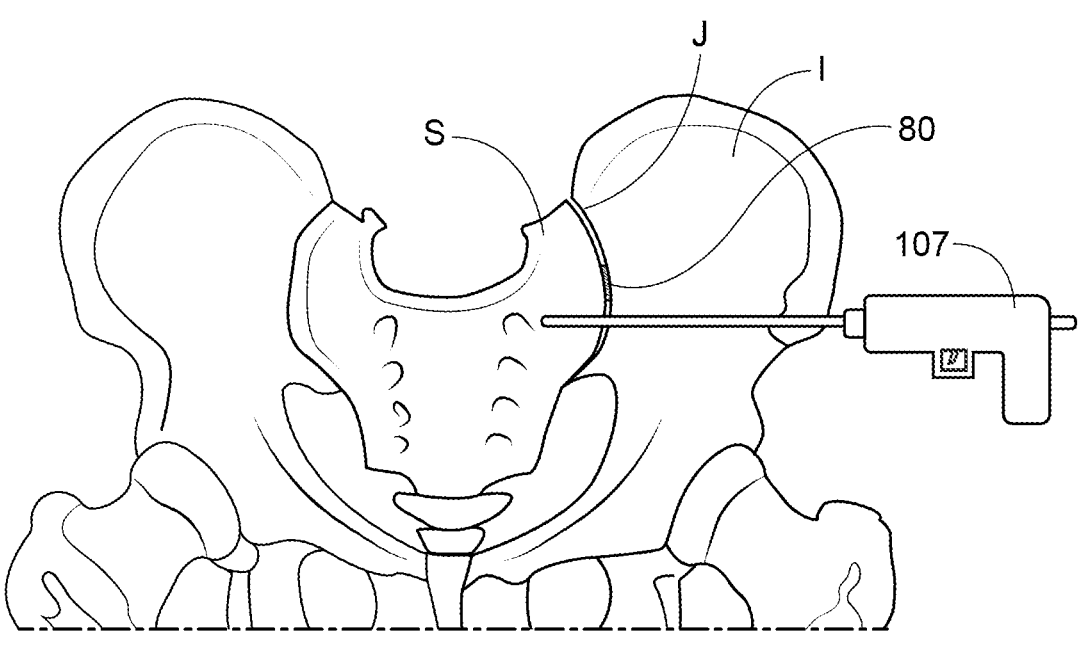
FIG. 17 is a schematic anterior view illustrating an instrument for preparing the joint space, according to an embodiment of the present disclosure.

Referring to FIG. 17, the method may then include drilling the bore using a drill 107 through the iliac bone I and another bore at the first location of the sacrum S. The bore may also be drilled using a reamer. The drill 107 or reamer may include a handle end and a driving end. The drill 107 may be used to slide along the guide pin and further form a bore into the iliac bone I and sacrum S. Further, the method may include drilling a bore via the drill 107 through the iliac bone I and another bore at the second location of the sacrum S.

In this phase of the procedure, a dilator (not shown) can be inserted into the superior and inferior drill guides and an innermost cannula can be removed. A guidewire is then inserted and drilled through the iliac crest through the SI joint and into the sacrum. Another cannula (not shown) is removed and a cannulated drill bit is used to drill, over the guidewire, through the iliac bone into the sacrum.

Figure 18:
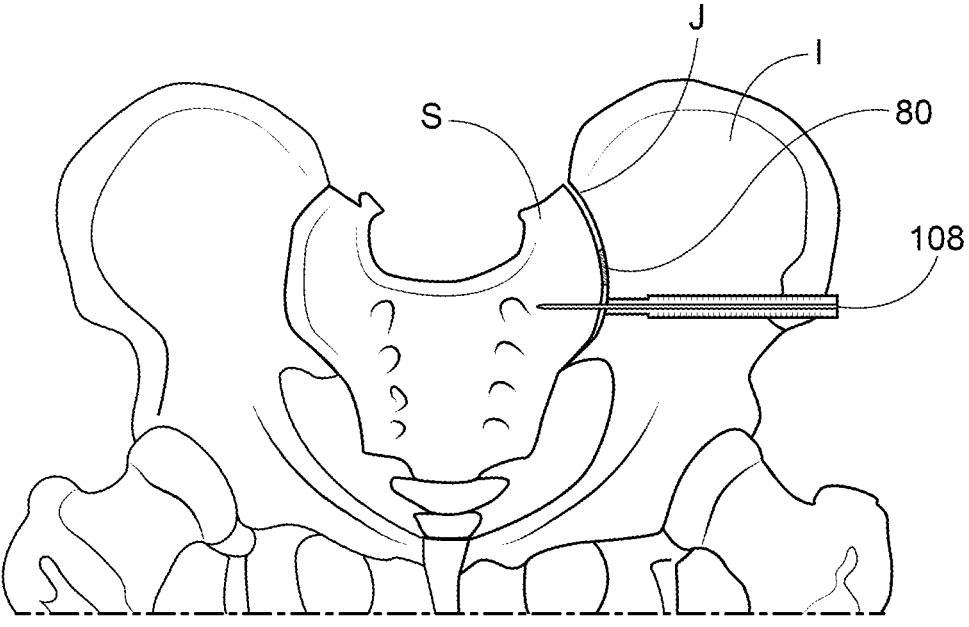
FIG. 18 is a schematic anterior view illustrating a depth gauge inserted toward the joint space, according to an embodiment of the present disclosure.

Referring to FIG. 18, a depth gauge 108 may be inserted into the bore(s) of the iliac bone I to assess the length of the anchor needed. The depth gauge 108 may be used to obtain a relative distance from the surface of the skin to a cortical surface of the iliac crest proximate the target location at the SI joint. The relative distance is used to help select the appropriate-sized anchors in the anchor system 20 for the intended procedure.

Figure 19:
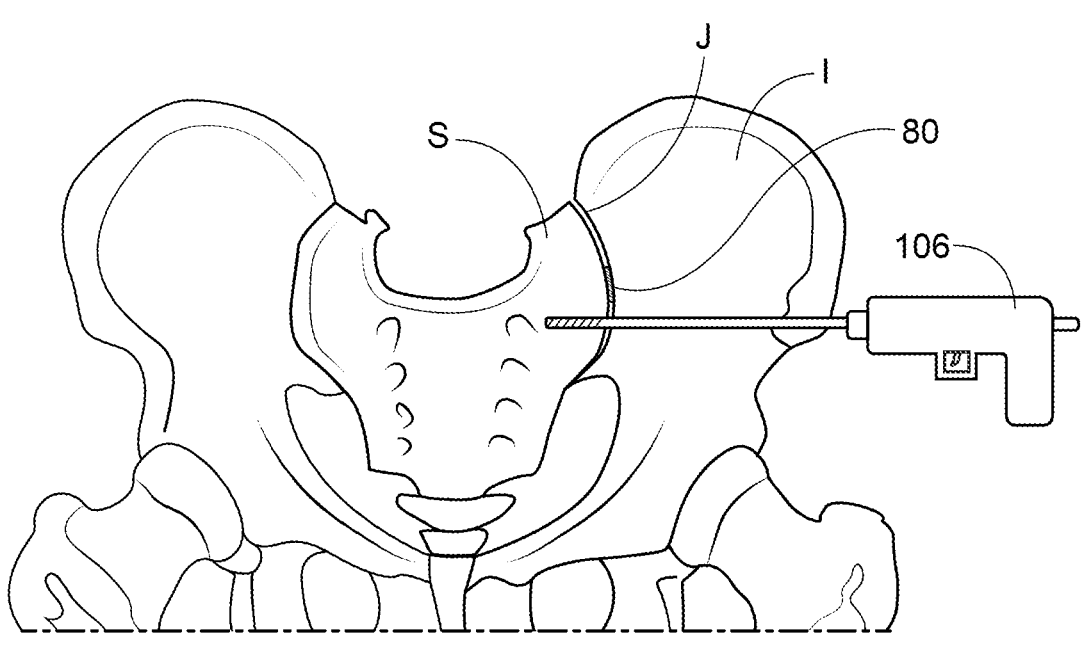
FIG. 19 is a schematic anterior view illustrating another instrument for preparing the joint space, according to an embodiment of the present disclosure.
Figure 20:
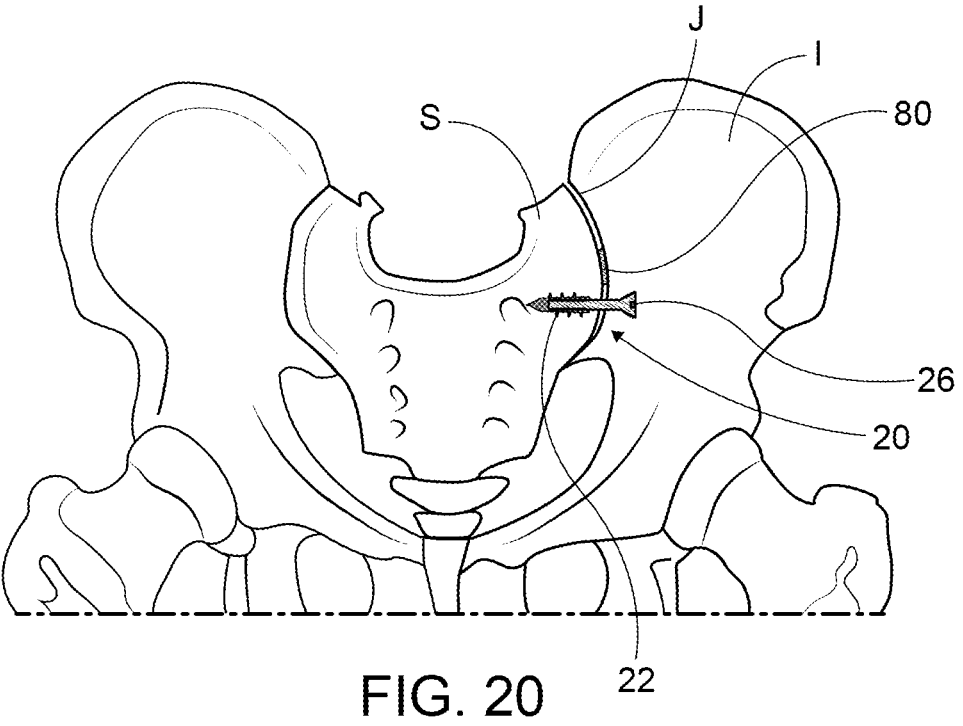
FIG. 20 is a schematic anterior view showing the compression anchor system shown in FIG. 1 secured across the sacroiliac joint.

Referring to FIGS. 19 and 20, a user may then couple the first sacrum anchor 22A to a first driving instrument. The method may then include advancing the first sacrum anchor 22A and the first driving instrument 106 through the first hole in the guide member 104 and toward the bore in the sacrum S. In this embodiment, the cannulation of the anchor slides along the guidewire into position in the bone. A user may then apply torque to the first sacrum anchor 22A with the first driving instrument 106 to threadably engage the external thread portion 38 of the first sacrum anchor 22A with the sacrum S. This would include advancing the first sacrum anchor 22A in a lateral direction across the SI joint J until a proximal end 28 of the first sacrum anchor 22A is substantially aligned with a surface of the sacrum S. Then, a user may advance a first compression anchor 26A through a first bore in the iliac bone I, along the guidewire, and across the SI joint J so that a) an outer thread portion 68 on a shaft 66 of the first compression anchor 26A engages an internal thread portion 44 of the first sacrum anchor 22A and b) a head of the first compression anchor 26A aligns and/or abuts with a surface of the iliac bone I.

A user may then apply torque to the head 64 of the first compression anchor 26A to cause the head 64 of the first compression anchor 26A and the iliac bone I to move closer to or further away from the proximal end 28 of the first sacrum anchor 22A. Thus, as the user rotates the instrument 106 in a first rotational direction, the first compression anchor 26A and the iliac bone I to move closer to the proximal end 28 of the first sacrum anchor 22A. As the user rotates the instrument 106 in a second rotational direction that is opposite the first rotational direction, the first compression anchor 26A and the iliac bone I move further away from proximal end 28 of the first sacrum anchor 22A. This process allows the user to dial in the needed compression of the SI joint J based on the clinical setting during the procedure.

Once a first anchor system 20A is in place, a second anchor system 20B may be implanted. In such an example, the method may include advancing a second sacrum anchor 22B along the lateral direction across the SI joint J to a second location in the sacrum S. In this example, the second location is opposite and spaced from the first location along the SI joint J. The method may further include threadably engaging an external thread portion 38 of the second sacrum anchor with the sacrum S until a proximal end 28 of the second sacrum anchor 22B is substantially aligned with the surface of the sacrum S at the second location. Next, a user may advance a second compression anchor 26B through a second bore in the iliac bone I and across the SI joint J so that a) an outer thread portion 68 on a shaft 66 of the second compression anchor 26B engages an internal thread portion 44 of the second sacrum anchor 22B and b) a head 64 of the second compression anchor 26B abuts the surface of the iliac bone I.

The method may then include applying torque to the head 64 of the second compression anchor 26B to cause the head 64 of the second compression anchor 26B and the iliac bone I to move closer to or further away from the proximal end 28 of the second sacrum anchor 22B. Thus, as the user rotates the instrument 106 in a first rotational direction, the second compression anchor 26B and the iliac bone I move closer to the proximal end 28 of the second sacrum anchor 22B. As the user rotates the instrument 106 in a second rotational direction that is opposite the first rotational direction, the second compression anchor 26B and the iliac bone I move further away from proximal end 28 of the second sacrum anchor 22B. This process allows the user to dial in the needed compression of the SI joint J based on the specific anatomic presentations that arise during the procedure, as discussed above. Indeed, a user can adjust the compression along each anchor system 20 as needed.

While the disclosure is described herein, using a limited number of embodiments, these specific embodiments are not intended to limit the scope of the disclosure as otherwise described and claimed herein. The precise arrangement of various elements and order of the steps of articles and methods described herein are not to be considered limiting. For instance, although the steps of the methods are described with reference to sequential series of reference signs and progression of the blocks in the figures, the method can be implemented in an order as desired

The invention claimed is:

1. A bone fixation system for compression of a sacroiliac joint defined between a sacrum and an iliac bone, the bone fixation system comprising:

a sacrum anchor that is elongate along a first central axis, the sacrum anchor having a proximal end, a distal end spaced from the proximal end along the first central axis, an external thread portion, an internal channel defined by an inner surface, the inner surface including an internal thread portion within the internal channel opposite the external thread portion, wherein the external thread portion is aligned with the internal thread portion along a radial direction that is substantially perpendicular to the first central axis; and a compression anchor configured for implantation through a bore in the iliac bone into engagement with the sacrum anchor, the compression anchor including a head having iliac-bone-engaging threads, a shaft that is elongate along a second central axis and that extends relative to the head, a cannulation that extends from the head to a distal end of the shaft, and an outer thread portion along part of the shaft, wherein the outer thread portion of the compression anchor is configured to threadably engage the internal thread portion of the sacrum anchor, wherein the external thread portion includes a plurality of external thread peaks and a first pitch that extends between first and second peaks of the plurality of external thread peaks, wherein the internal thread portion includes a plurality of internal thread peaks and a second pitch that extends between first and second peaks of the plurality of internal thread peaks, wherein the first pitch is greater than the second pitch, wherein rotation of the compression anchor about the second central axis draws the head of the compression anchor closer to or further away from the sacrum anchor when the outer thread portion of the compression anchor is threadably engaged with the internal thread portion of the sacrum anchor.

2. The bone fixation system of claim 1, wherein a substantial entirety of the external thread portion is aligned with a substantial entirety of the internal thread portion.

3. The bone fixation system of claim 1, wherein the internal thread portion extends along a first length of the inner surface, and the outer thread portion of the compression anchor extends along a second length of the shaft, wherein the first length and the second length are substantially the same.

4. The bone fixation system of claim 1, wherein the internal thread portion extends along a first length of the inner surface, and the outer thread portion of the compression anchor extends along a second length of the shaft, wherein the first length is between about 5 mm and 20 mm, and the second length is between about 5 mm and 20 mm.

5. The bone fixation system of claim 1, wherein the shaft of the compression anchor includes a smooth surface that extends from a distal-most end of the head to the outer thread portion.

6. The bone fixation system of claim 1, wherein the shaft defines a shaft length that extends from the head to the distal end along the second central axis, wherein the outer thread portion has a length that is no greater than half of the shaft length.

7. The bone fixation system of claim 1, wherein the head of the compression anchor defines an outer head diameter that is substantially perpendicular to the second central axis, and the external thread portion of the sacrum anchor defines a maximum external diameter that is perpendicular to the first central axis, wherein the outer head diameter is substantially similar to the maximum external diameter.

8. The bone fixation system of claim 1, wherein the external thread portion of the sacrum anchor defines a maximum external diameter that is perpendicular to the first central axis, and the maximum external diameter is between about 5 mm and about 20 mm.

9. The bone fixation system of claim 1, wherein the head of the compression anchor defines an outer head diameter that is perpendicular to the second central axis, and the outer head diameter is between 5 mm and 20 mm.

10. The bone fixation system of claim 1, wherein the head of the compression anchor defines an outer head diameter that is perpendicular to the second central axis, and the shaft defines an outer shaft diameter that is parallel to the outer head diameter, wherein the outer head diameter is at least 1.25 times the outer shaft diameter.

11. The bone fixation system of claim 1, further comprising:

a working cannula that is elongate along an insertion axis, the working cannula having a proximal end, a distal end spaced from the proximal end along the insertion axis, and a channel that extends from the proximal end toward the distal end along the insertion axis; and an outrigger having an insertion arm that extends along a first direction, a lateral arm that extends along a second direction that is perpendicular to the first direction, and a guide arm coupled to the lateral arm and spaced from the insertion arm along the second direction, the insertion arm being insertable into the channel along the insertion axis so as to inhibit movement of the outrigger relative to the working cannula along directions that are substantially perpendicular to the insertion axis when the insertion arm of the outrigger is inserted into the channel of the working cannula, wherein the guide arm defines one or more holes that are sized and configured to receive therethrough the sacrum anchor and the compression anchor.

12. The bone fixation system of claim 11, wherein the distal end of the working cannula defines a first tine and a second tine positioned relative to each other to orient the working cannula at a target location of the sacroiliac joint along the insertion axis.

13. The bone fixation system of claim 11, wherein the distal end of the working cannula is configured to carry an implant therein.

14. The bone fixation system of claim 11, wherein the proximal end defines a first cross-sectional shape of the channel, wherein the insertion arm defines an insertion end having a second cross-sectional shape configured to mate with the first cross-sectional shape of the channel so that the insertion arm is insertable into the channel along the insertion axis.

15. The bone fixation system of claim 14, wherein the first and second cross-sectional shapes are sized so as to inhibit any lateral movement of the outrigger relative to the working cannula when the outrigger is inserted into the working cannula.

16. The bone fixation system of claim 15, wherein the second cross-sectional shape is not circular.

17. The bone fixation system of claim 15, wherein the one or more holes include a first hole that extends along a first hole axis and a second hole that extends along a second hole axis, the first and second holes being oriented such that the first and second hole axes are aligned with the first direction and intersect distal end of the working cannula when the insertion arm is fully seated in the channel of the working cannula.

* * * * *